United States Patent [19]
Ulich

[11] Patent Number: 5,376,368
[45] Date of Patent: * Dec. 27, 1994

[54] COMPOSITION AND METHOD FOR TREATING INFLAMMATION

[75] Inventor: Thomas R. Ulich, Wildomar, Calif.

[73] Assignee: Regents of University of California, Alameda, Calif.

[*] Notice: The portion of the term of this patent subsequent to Apr. 5, 2011 has been disclaimed.

[21] Appl. No.: 186,762

[22] Filed: Jan. 25, 1994

Related U.S. Application Data

[63] Continuation of Ser. No. 989,959, Dec. 10, 1992, Pat. No. 5,300,292, which is a continuation of Ser. No. 695,548, May 3, 1991, abandoned.

[51] Int. Cl.$^5$ .......................... A61K 37/02; C07G 7/00
[52] U.S. Cl. ........................................ 424/85.2; 514/2; 514/21
[58] Field of Search ...................... 514/2, 21; 424/85.2

[56] References Cited

U.S. PATENT DOCUMENTS

| | | | |
|---|---|---|---|
| 4,806,523 | 2/1989 | Bentz et al. | 514/2 |
| 4,971,952 | 11/1990 | Bentz et al. | 514/2 |
| 4,973,478 | 11/1990 | Gauldie et al. | 424/85.4 |
| 4,975,467 | 12/1990 | Ku et al. | |
| 5,300,292 | 4/1994 | Ulich | 424/85.2 |

FOREIGN PATENT DOCUMENTS

| | | |
|---|---|---|
| 0128849 | 6/1984 | European Pat. Off. |
| 8401106 | 3/1984 | WIPO |

OTHER PUBLICATIONS

Aderka, et al. *J. of Immunology* 143 (11): 3517–3523 (1989).
Dunham et al. *J. of Leukocyte Biology* 48: 473–481 (1990).
Ulich et al. *J. of Immunology* 146 (7): 2316–2323 (1991).
Ulich et al. *Amer. J. of Pathology* 137 (5): 1173–1185 (1990).
Blaug, *Medicated Applications*, "Remington's Pharmaceutical Sciences", Chapter 87: 1523–1553.
Hirano et al. *Nature* 324 (6): 73–76 (1986).
Castell et al. *Eur. J. Biochem.* 177: 357–361 (1988).
Northemann et al. *J. of Biological Chem.* 264 (27): 16072–16082 (1989).
Barton et al. Protective Role of Inrterleukin 6 in the Lipopolysaccharide–Galactosamine Septic Shock Model, Infection and Immunity: 1496–1499 (1993).
Tilg et al. Interleukin-6 (IL–6) As an Anti-Inflammatory Cytokine: Induction of Circulating IL–1 Receptor Antagonist and Soluble Tumor Necrosis Factor Receptor p55, *Blood.* 83: 113–118 (1994).

*Primary Examiner*—Howard E. Schain
*Assistant Examiner*—P. Lynn Touzeau
*Attorney, Agent, or Firm*—Knobbe, Martens, Olson & Bear

[57] ABSTRACT

A method for treatment of inflammation, comprising the step of administering to a patient in need thereof an effective, inflammation-inhibiting amount of a composition comprising IL-6, or IL-6 and TGF$\beta$ together in a weight ratio of from about 5:95 to 95:5, preferably from about 20:80 to 80:20. Also disclosed is a composition for treatment of inflammation, comprising as active ingredients IL-6 and TGF$\beta$ in a weight ratio of from about 5:95 to about 95:5, optionally comprising a carrier in combination with the active ingredients, and a method of reducing migration of neutrophils into tissue of an animal which has received an inflammatory stimulus, comprising the step of administering to the tissue an effective neutrophil-migration-inhibiting amount of a composition as defined above.

7 Claims, No Drawings

COMPOSITION AND METHOD FOR TREATING INFLAMMATION

GOVERNMENT INTEREST IN INVENTION

This invention was made with Government support under Grant No. R01-AI-26551, awarded by the National Institutes of Health. The Government has certain rights in this invention.

This application is a continuation of application Ser. No. 07/989,959, filed Dec. 10, 1992, now U.S. Pat. No. 5,5300,292, which is a continuation of Ser. No. 07/695,548, filed May 3, 1994, now abandoned.

FIELD OF THE INVENTION

The present invention relates to treatment of inflammation, and more particularly to compositions of interleukin-6 and transforming growth factor beta used in treatment of inflammation.

BACKGROUND OF THE INVENTION

During acute inflammatory reactions, leukocytes and serum molecules are relocated to areas of damage in the body. These areas of damage are often associated with physical injury. Upon injury, the clotting system and plasmin systems are initiated together with the appropriate nervous system response to generate an initial response to facilitate immune activation. Increased blood flow, capillary permeability and chemotactic factors, including those of the complement cascade, modulate neutrophil migration to the damaged site. Neutrophils are the predominant cell type involved in acute inflammation, whereas lymphocytes and macrophages are more prevalent in chronic inflammation.

Cytokines are proteins from inflammatory and parenchymal cells that regulate the immune response. T cells, macrophages, and B cells all produce and respond to the appropriate cytokines. Neutrophils are also activated in response to cytokines. While activation of the appropriate inflammatory pathways is necessary for an effective inflammatory response, there can also be negative aspects to cytokine-mediated cell activation.

Two cytokines, TNF (tumor necrosis factor) and IL-1 (Interleukin-1) upregulate the acute inflammatory pathway. These molecules influence cell migration as well as many of the pathophysiologic responses associated with the acute inflammatory reaction. IL-1 and TNF, together with other cytokines, can also induce systemic effects including neutrophilia, lymphopenia, fever, and hypotensive shock.

Gram-negative bacteria have a proinflammatory lipopolysaccharide component (LPS) of their cell walls that is a potent endotoxin. Activation of acute inflammation in response to the endotoxin, LPS, is primarily orchestrated by cytokines. This endotoxin upregulates IL-1 and TNF. Over-activation of the acute inflammatory response via IL-1 and TNF can lead to negative local effects such as abscess formation with irreversible parenchymal damage and sometimes life-threatening systemic side effects such as hypotensive shock.

Over-expression of TNF and IL-1 produces a shock syndrome as observed when pure TNF or IL-1 are administered to experimental animals. Administration of TNF and IL-1 in high doses induces hypotension, metabolic acidosis and multiple end-organ damage similar to that observed in endotoxin-induced shock.

Similar responses are also observed in acute inflammatory reactions in humans, particularly when the stimulatory signal required to initiate the inflammatory reaction is sufficiently large. Intense inflammatory responses to invasive organisms can cause tissue injury and patient mortality.

Acute inflammatory reactions are often initiated by invasive organisms and injury; however, there are many other disease states characterized by acute inflammation.

It is with this in mind that physicians attempt to control the acute inflammatory reaction with glucocorticoids, nonsteroidal anti-inflammatory agents and cytotoxic drugs. These general immunosuppressive agents are helpful but are not specifically directed to the resolution of the acute inflammatory response. Agents specifically directed to the control of the acute reaction would be less likely to promote the systemic side effects produced by general immunosuppressives and would permit better control over a potentially life-threatening reaction. Inhibitors of acute inflammation with fewer side effects would therefore be most useful.

The role of TGF$\beta$ (Transforming growth factor-beta) in acute inflammation has not been defined. TGF$\beta$ is present in a variety of cell types including activated macrophages. It is known that TGF$\beta$ can have both growth stimulatory and inhibitory activities on cell proliferation. TGF$\beta$ is also a potent immunosuppressive factor. It is present in rheumatoid synovial fluids and can inhibit IL-1 induced lymphocyte proliferation. Additionally, TGF$\beta$ can suppress production of TNF$\alpha$ from LPS-stimulated macrophages.

U.S. Pat. Nos. 4,806,523 and 4,971,952 teach the use of TGF$\beta$ to treat inflammation reactions such as those resulting from viral, bacteria fungal or autoimmune processes. As shown in the laboratory and in the experimental results disclosed herein, TGF$\beta$ is helpful but not always sufficient to control acute inflammatory reactions. Therefore, substances that could work alone or together with TGF$\beta$ to downregulate the inflammatory reaction would provide a more effective anti-inflammatory therapy.

Interleukin-6 (IL-6) is a cytokine that is known to induce terminal differentiation in B cells, stimulate T cell proliferation and induce the differentiation of hemopoietic stem cells. IL-6 is produced in a variety of cells including fibroblasts and monocytes. Intravenous IL-6 was reported to decrease intravenous endotoxin induced serum TNF levels in mice (Aderka et al. J. Immunol. 143:3517. 1989) and in rats (Ulich et al.; J. Immunol. (in press)). However, IL-6 is also reported to induce acute phase inflammatory responses (Castell et al.; Eur. J. Biochem 177:357–361 1988). Il-6 is known to have immuno-modulating activity, but its precise behavior in acute inflammation is not known.

The control of the acute inflammatory reaction can present significant problems to physicians. General immunosuppressive agents may not sufficiently control the acute reaction and may further hinder the resolution of the initial causative insult. The suppression of wound repair and decreased clearance of adventitious agents are two potential side effects of generalized immunosuppression.

It is an object of the invention to provide a method for controlling inflammation, and particularly for controlling the acute inflammatory reaction.

It is a further object of the invention to provide a method and composition that is nonsteroidal, and that is more effective than TGF$\beta$ alone.

These and other objects and advantages of the present invention will be apparent in the detailed description of the invention that follows.

SUMMARY OF THE INVENTION

The present invention includes a method for treatment of inflammation, comprising the step of administering to a patient in need thereof an effective, inflammation-inhibiting amount of a composition comprising IL-6 alone or IL-6 and TGFβ respectively in a weight ratio of from about 5:95 to 95:5. In one embodiment, the weight ratio of IL-6 to TGFβ is from about 20:80 to 80:20. The method is used to treat acute inflammation, although treatment of chronic inflammation will also occur since chronic inflammation has been proven to follow the acute inflammatory response. The administering step may comprise injecting the composition into the patient intravenously, intradermally, subcutaneously, intraarticularly, intraperitoneally or otherwise, introducing the composition into the bronchial passageway, applying the composition topically, as a suppository, or implanting the composition In one embodiment, the patient is given a daily combined dosage of IL-6 or IL-6 and TGFβ of about 0.5 μg/kg to about 1000 μg/kg. The preferred dosage is from about 1 μg/kg to about 250 μg/kg.

Also provided as a part of the invention is a composition for treatment of inflammation, comprising as active ingredients IL-6 and TGFβ in a weight ratio of from about 5:95 to about 95:5, optionally comprising a carrier in combination with the active ingredients. The composition may, for example, include as carriers a sterile injectable carrier, a dermatologically acceptable topical carrier, an implantable carrier, or an atomizable inhalable carrier. In a preferred composition, the ratio of IL-6 to TGFβ is from about 20:80 to about 80:20.

The present invention also includes a method of reducing migration of neutrophils into tissue of an animal which has received an inflammatory stimulus, comprising the step of administering to the tissue an effective neutrophilmigration-inhibiting amount of a composition comprising as active ingredients IL-6 alone or IL-6 combined with TGFβ in a weight ratio of from about 5:95 to about 95:5. In this method as well, the composition may be administered directly to the involved tissue, or may be administered systemically. The weight ratio of IL-6 to TGFβ is preferably from about 20:80 to about 80:20.

DETAILED DESCRIPTION OF THE INVENTION

The nature of the endogenous mediators that downregulate and put an end to the exodus of neutrophils into local acute inflammatory sites is unknown. The present invention is based on the discovery that interleukin-6 (IL-6) and transforming growth factor-β (TGFβ), members of a family of macrophage-derived proteins known as cytokines, in combination, significantly inhibit the acute neutrophilic exodus caused by an intratracheal injection of endotoxin (LPS), a proinflammatory component of the cell walls of gramnegative bacteria. Treatment of inflammation, as used herein, includes prophylaxis as well as treatment of an existing condition.

TGFβ (10 μg) and IL-6 (10 μg) coinjected intratracheally with LPS (10 μg) each inhibited the number of neutrophils in six hour bronchoalveolar lavage (BALL) specimens by approximately 50%.

Surprisingly, the intratracheal coinjection of IL-6, TGFβ, and LPS inhibited the LPS-induced neutrophilic inflammatory exodus by nearly 75%. The magnitude of this antiinflammatory effect is approximately the same as that provided by a maximum dose of the powerful steroidal antiinflammatory agent, dexamethasone, as shown in parallel experiments (Example 4).

IL-6 is also shown to be endogenously upregulated within the lung after intratracheal challenge with endotoxin, providing evidence that IL-6 may represent an endogenous negative feedback mechanism to inhibit endotoxin-initiated cytokine-mediated acute inflammation. IL-6 and TGFβ both strongly inhibit the quantity of TNFα recovered in the BAL fluid of LPS-challenged rate, suggesting that downregulation of LPS-induced TNFα production within the lung represents one mechanism whereby IL-6 and TGFβ exert an antiinflammatory action. It is proposed that IL-6 and TGFβ are endogenous inhibitors of acute inflammation.

Thus, the present invention resides in the administration of IL-6, or the coadministration of IL-6 and TGFβ to produce a more powerful antiinflammatory action than is provided by either agent alone.

TGFβ may be obtained by extraction and purification from natural sources, such as bovine kidney, human placenta, and human platelets. Processes for obtaining TGFβ are disclosed, for example, in published PCT application PCT/US83/01460, published as WO84/01106, and published European application EPA 84450016.5, published Dec. 19, 1984, publication No. 0128849. Alternatively, TGFβ may be synthesized or produced by recombinant DNA techniques. The amino acid sequence of platelet-derived human TGFβ is disclosed, for example, in U.S. Pat. No. 4,971,952.

Interleukin-6 is also available from a variety of sources. The structure of the human c-DNA is disclosed, for example, by Mirano, et al., *Nature* 324:73 (1986). The structure of the rat c-DNA is disclosed by W. Northemann, et al., *J. Bio. Chem.* 264:16072 (1990). Moreover, recombinant IL-6 is manufactured by Amgen, Inc., Thousand Oaks, Calif.

As used herein, the terms IL-6 and TGFβ are functional descriptions of molecules and cover and include the human and other vertebrate forms of these proteins. In addition, they cover functionally equivalent modified molecules, such as active antiinflammatory fragments of the natural material, and molecules having substantial (i.e., 90%) amino acid homology with the natural materials which retain the antiinflammatory activity of those natural materials.

In the compositions of the present invention where IL-6 is conjoined with TGFβ, the active ingredients IL-6 and TGFβ are combined in a weight ratio of from about 5:95 to 95:5, preferably from about 20:80 to 80:20, and more preferably in roughly equal weight ratios, i.e., about 50:50 or about 40:60 to about 60:40.

The compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000. Preparation of compositions for local use are detailed in Remington's Pharmaceutical Sciences, 15th Edition, 1523-1553 (Mack Publishing, 1975).

When the composition is to be used as an injectable material, it can be formulated into a conventional injectable carrier. Suitable carriers include biocompatible and pharmaceutically acceptable phosphate buffered saline solutions, which are preferably isotonic.

As an atomizable composition, or a lavage, the active ingredients of the present invention may be administered to treat diseases of the lungs. Diseases of the lungs involving inflammation include asbestosis, silicosis, coal miner's pneumoconiosis; those relating to autoimmune conditions that may involve the lungs include rheumatoid arthritis, lupus erythematosus; and granulomatous inflammations of the lungs include Wegener's granulomatosis and eosinophilic granulomatosis.

Topical indications include contact dermatitis, psoriasis vulgaris, dermal ulcers, and acute or chronic eczematous dermatitis.

The compositions of the present invention that are intended for systemic use will generally contain sufficient active ingredient to deliver from about 0.1 $\mu$g/kg to about 1000 $\mu$g/kg (weight of active ingredient/body weight of patient). Preferably, the composition will deliver at least 0.5 or 1.0 $\mu$g/kg, and more preferably at least 2, 3, 5, or 10 $\mu$g/kg. As an upper limit, the preferred composition will deliver up to 500, more preferably up to 300 or 200 $\mu$g/kg of active ingredient. The foregoing amounts apply both to IL-6 alone and IL-6 combined with TGF$\beta$.

Practice of the method of the present invention comprises administering to a patient an effective amount of the active ingredient(s), in any suitable systemic or local formulation, in an amount effective to deliver the dosages listed above. An effective, particularly preferred dosage for substantially inhibiting neutrophil influx in response to inflammatory stimulus is 30–100 $\mu$g/kg. The dosage can be administered on a one-time basis, or (for example) from one to 5 times per day.

Although the invention is particularly suitable for cases of acute inflammation, it also has utility for chronic inflammation. Types of inflammation that can be treated with the present invention include diffuse inflammation, traumatic inflammation, immunosuppression, toxic inflammation, specific inflammation, reactive inflammation, parenchymatous inflammation, obliterative inflammation, interstitial inflammation, croupous inflammation, and focal inflammation.

EXAMPLE 1

Inhibition of Neutrophilic Inflammatory Exodus

Rats (congenic male Lewis rats weighing approximately 225 grams and anaesthetized with ether) were injected intratracheally with equal volumes (0.5 ml) of various doses and combinations of either endotoxin (S. Typhus lipopolysaccharide, Sigma Chem. Co., St. Louis, Mo.), recombinant human IL-6, or recombinant human TGF$\beta$ (Amgen, Inc., Thousand Oaks, Calif.). Six hours later, the rats were sacrificed and bronchoalveolar lavage (BAL) via the instillation of a tracheal catheter was preformed to enumerate the absolute number of neutrophils in the intraalveolar inflammatory exudate. The six hour timepoint has been determined to represent the peak of the neutrophilic inflammatory exodus. Experiments were preformed by randomly dividing rats into experimental groups to be injected on the same day with either LPS or with LPS plus IL-6 or TGF$\beta$. A typical day's experiment consisted of injecting three rats intratracheally with LPS alone and 3 rats intratracheally with LPS plus a cytokine. The absolute number of neutrophils in the BAL specimens of the rats from each experimental group is expressed as the mean plus-or-minus one standard error of the mean. The p-value was determined by the two-tailed t-test for unpaired data. Histologic examination of the Bouin's-fixed paraffin-embedded sections of the lungs after BAL was performed to evaluate the accumulation of neutrophils within pulmonary parenchyma and the adequacy of BAL. TNF protein determinations in BAL fluid was determined as described by Ulich, et al., *Am. J. Pathol.* 137:1137–1185 (1990). Whole lung RNA extraction, Northern blotting, and hybridization for IL-6 mRNA were performed as described therein.

The LPS-induced acute inflammatory exodus was inhibited by an average of 61% in rats receiving 10 $\mu$g IL-6 plus 1 $\mu$g LPS 9n-7) as opposed to rats receiving 1 $\mu$g LPS alone (n=9) (p<0.0001, Table 1). The LPS-induced neutrophilic exodus was inhibited by an average of 53% in rats receiving 10 $\mu$g IL-6 plus 10 $\mu$g LPS (n=18) as opposed to rats receiving 10 $\mu$g LPS alone (n=18) (p<0.0001, Table 1). Intratracheal injection of IL-6 alone caused the accumulation of a very small number of neutrophils (less than $10^6$ neutrophils/BAL, n=2). Intratracheal injection of saline causes no or at most a very slight accumulation of neutrophils in BAL fluid.

The LPS-induced acute inflammatory exodus was inhibited by an average of 54% in rats receiving 10 $\mu$g TGF$\beta$ plus 10 $\mu$g LPS (n=13+ as opposed to rats receiving 10 82 g LPS alone (n=14) (p<0.0001, Table 1). The LPS-induced accumulation of neutrophils was inhibited by 35% in rats receiving 1 $\mu$g TGF$\beta$ plus 10 $\mu$g LPS (n=6) as opposed to rats receiving 10 $\mu$g LPS alone (n=6) (p<0.02, Table 1). Intratracheal injection of TGF$\beta$ alone did not cause a significant influx of neutrophils into the lungs (less than $0.1 \times 10^6$ neutrophils/BAL).

EXAMPLE 2

Combined Effects of IL-6 and TGF$\beta$

The combined effects of IL-6 and TGF$\beta$ on LPS-induced acute neutrophilic inflammation were investigated using the procedures set forth in Example 1. All four experimental groups (10 $\mu$g LPS alone, 10 $\mu$g LPS plus 10 $\mu$g IL-6, 10 $\mu$g LPS plus 10 $\mu$g TGF$\beta$, and 10 $\mu$g LPS plus 10 $\mu$g IL-6 plus 10 $\mu$g TGF$\beta$) were concurrently studied. The combination of IL-6 plus TGF$\beta$ inhibited the LPS-induced neutrophilic exodus by 74% as opposed to 35% inhibition with IL-6 alone and 56% inhibition with TGF$\beta$ alone (Table II). The combined inhibitory effect of IL-6 with TGF$\beta$ was significantly greater than the inhibitory effect of either cytokine alone (p<0.008).

Histologic examination of the lungs in all four experimental groups (n=2 rats from each group) was performed after BAL to exclude the possibility that the decrease in BAL neutrophils might be due to an increase in neutrophils remaining in the lungs of cytokine-treated rats (as might occur, for example, if IL-6 or TGF$\beta$ induced the expression of adhesion molecules that caused the neutrophils to adhere more avidly to pulmonary parenchyma). Double-blind microscopic evaluation of the lungs revealed an indistinguishable histologic appearance in the LPS plus cytokine-treated groups. The LPS alone-treated group was distinguished from the other three groups by a greater number of neutrophils. One may therefore conclude that the degree of cytokine-induced inhibition of acute neutrophilic inflammation as measured by BAL is, if anything, an underestimation of the true amount of inhibition. The LPS-induced inflammatory reaction was histologically characterized by the appearance of a modest number of neutrophils in alveolar spaces, alveolar spaces, and in bronchial mucosa as previously illustrated by my laboratory. TNF protein levels in the BAL fluids of the same rats were measured and were found to be decreased by 66% in both LPS plus IL-6 and LPS plus TGF-treated rats and to be decreased by 88% in LPS IL-6 plus TGF$\beta$-treated rats as compared to LPS alone-treated rats (274±30 U TNF/BAL after LPS alone, 94±36 U TNF/BAL after LPS plus IL-6, 96±38 U TNF/BAL after LPS plus TGF$\beta$ and 34±17 U TNF/BAL after LPS plus IL-6 plus TGF$\beta$.

EXAMPLE 3

Comparison to Antiinflammatory Activity of Dexamethasone

The procedure of Example 1 was repeated, using the potent steroidal antiinflammatory material dexamethasone. The results are as follows: 10 $\mu$g dexamethasone inhibited LPS-induced neutrophilic inflammation by 48%; 100 $\mu$g dexamethasone inhibited LPS-induced neutrophilic inflammation by 67%, and 1000 $\mu$g dexamethasone inhibited LPS-induced neutrophilic inflammation by 79%. The latter dose of dexamethasone is at the upper limits of toxicity for human use.

Thus, the present invention inhibits LPS-induced acute inflammation to approximately the same degree as the maximum dose of dexamethasone. It is believed that the cytokines of the present invention can inhibit such inflammation more safely and with significantly less serious systemic side effects than dexamethasone.

EXAMPLE 4

Demonstration of IL-6 mRNA Expression in Response to LPS Injection

IL-6 mRNA expression was determined in whole lung RNA extracts by Northern blotting using a rat IL-6 cDNA probe at sequential timepoints after the intratracheal or intravenous injection of 100 $\mu$g LPS. Intratracheal injection of LPS caused IL-6 mRNA expression beginning at 2 hours and increasing markedly at 4 hours. In a further study of pulmonary IL-6 mRNA expression at later timepoints after intratracheal injection of LPS, IL-6 mRNA expression was found to remain at a very high level at 6 hours with a return to preinjection levels at 12, 24, and 48 hours. In contrast to the kinetics of IL-6 expression after the intratracheal injection of LPS, intravenous injection of LPS caused IL-6 mRNA expression peaking at 2 hours with a substantial decrease towards baseline level by 4 hours.

These experiments strongly suggest that IL-6 is an endogenous local downregulator of inflammation.

In the preceding examples, IL-6 alone and IL-6 and TGF$\beta$ in combination are shown to strongly inhibit LPS-induced acute inflammation. These compositions thus represent novel antiinflammatory pharmaceuticals having therapeutic utility in clinical situations of cytokine-mediated acute inflammation. The activity of these combined cytokines at 10$\mu$g is approximately equal to that of the maximum dose of the potent steroidal antiinflammatory agent dexamethasone. The activity of 10$\mu$g IL-6 alone is approximately equal to that of an equivalent amount of dexamethasone.

The mechanism of the antiinflammatory action of IL-6 and TGF$\beta$ may relate to the ability of these cytokines to inhibit TNF$\alpha$ and IL-1 production by macrophages; however, the present invention is not to be limited to this particular theory of operation. Host-derived IL-6 is upregulated locally after challenge with LPS and may act as an endogenous inhibitor of acute inflammation. TGF$\beta$ is known to be a pleiotropic mediator and may be hypothesized to perform a dual role by acting both to resolve acute inflammation and to begin tissue repair and remodeling by initiating collagen deposition.

Although the invention has been described in the context of particular experiments and preferred embodiments, the scope of the invention is to be determined by reference to the claims that follow, including reasonable equivalents thereof:

What is claimed is:

1. A method for reducing migration of neutrophils in response to a localized inflammatory stimulus in a patient, comprising the step of administering to a patient in need thereof an effective, neutrophil-migration-inhibiting amount of a composition comprising as active ingredient IL-6.

2. The method of claim 1, wherein said patient is given a daily dosage of IL-6 of about 0.5 $\mu$g/kg to about 1000 $\mu$g/kg.

3. The method of claim 2, wherein said dosage is from about 1 $\mu$g/kg to about 250 $\mu$g/kg.

4. The method of claim 1, wherein said administering step comprises topically administering the composition to the patient.

5. The method of claim 1, wherein said administering step comprises introducing the composition into the patient's bronchial passageway.

6. A method of reducing migration of neutrophils into tissue of an animal in response to an inflammatory stimulus to such tissue, comprising the step of administering to said tissue an effective neutrophil-migration-inhibiting amount of a composition comprising as active ingredient IL-6.

7. The method of claim 6, wherein said composition is administered directly to said tissue.

* * * * *